United States Patent
Ramachandran (10) Patent No.: US 12,172,952 B2
(45) Date of Patent: Dec. 24, 2024

(54) ETHYLENE MAXIMIZATION WITH PROPYLENE METATHESIS

(71) Applicant: LUMMUS TECHNOLOGY LLC, Houston, TX (US)

(72) Inventor: Bala Ramachandran, Easton, PA (US)

(73) Assignee: Lummus Technology LLC, Houston, TX (US)

( * ) Notice: Subject to any disclaimer, the term of this patent is extended or adjusted under 35 U.S.C. 154(b) by 0 days.

(21) Appl. No.: 18/160,846

(22) Filed: Jan. 27, 2023

(65) Prior Publication Data

US 2023/0167040 A1    Jun. 1, 2023

Related U.S. Application Data

(62) Division of application No. 17/100,683, filed on Nov. 20, 2020, now Pat. No. 11,565,985.

(60) Provisional application No. 62/938,002, filed on Nov. 20, 2019.

(51) Int. Cl.
*C07C 4/06* (2006.01)
*C07C 11/04* (2006.01)
*C07C 11/06* (2006.01)
*C07C 11/08* (2006.01)

(52) U.S. Cl.
CPC ............. *C07C 4/06* (2013.01); *C07C 11/04* (2013.01); *C07C 11/06* (2013.01); *C07C 11/08* (2013.01)

(58) Field of Classification Search
CPC ........... C07C 4/02; C07C 4/06; C07C 5/2512; C07C 6/04
See application file for complete search history.

(56) References Cited

U.S. PATENT DOCUMENTS 3,261,879 A * 7/1966 Banks ................... C07C 6/04
                                                208/123
2015/0141722 A1 * 5/2015 Ramachandran ...... C07C 6/04
                                                585/315

* cited by examiner

*Primary Examiner* — Sharon Pregler
(74) *Attorney, Agent, or Firm* — Osha Bergman Watanabe & Burton LLP (57) ABSTRACT

Systems and processes herein improve the conversion of propylene to ethylene via metathesis. On a mass basis, embodiments herein may be used to convert greater than 40% propylene, on a mass basis, to ethylene, such as 43% to 75%, on a mass basis. In one aspect, processes for the conversion of propylene to ethylene herein may include introducing a propylene feed stream to a metathesis reactor, and contacting the propylene with a metathesis catalyst in the metathesis reactor to convert the propylene to ethylene and 2-butene. An effluent from the metathesis reactor may be recovered, the effluent including ethylene, 2-butene, and unconverted propylene. The effluent may then be separated in a fractionation system to recover an ethylene fraction, a propylene fraction, a c4 fraction, and a C5+ fraction. The propylene fraction and the C4 fraction may then be fed to the metathesis reactor to produce additional ethylene.

19 Claims, 6 Drawing Sheets

ETHYLENE MAXIMIZATION WITH PROPYLENE METATHESIS

FIELD OF THE DISCLOSURE

Embodiments herein relate to the conversion of propylene to ethylene. More specifically, embodiments herein relate to processes and systems for maximizing the conversion of propylene to ethylene via metathesis.

BACKGROUND

The products of propylene autometathesis are ethylene and n-butenes. Propylene metathesis creates one mole of ethylene (28 g/mol) from two moles of propylene (42 g/mol +42 g/mol). N-butenes (56 g/mol) as the second product is less valuable. On a mass basis, complete conversion of propylene results in only 33.3% of the propylene converting to ethylene, and the rest is n-butenes. Thus, even with a C3 recycle, the conversion of propylene feed to ethylene is necessarily less than 35%, on a mass basis.

SUMMARY OF THE DISCLOSURE

Systems and processes herein have been developed to improve the conversion of propylene to ethylene via metathesis. On a mass basis, embodiments herein may be used to convert greater than 40% propylene, on a mass basis, to ethylene. In some embodiments, the conversion of propylene to ethylene may be in the range of 43% to 75%, on a mass basis, such as greater than 45%, greater than 50%, greater than 60%, or greater than 65% on a mass basis in various embodiments.

In one aspect, embodiments herein relate to processes for the conversion of propylene to ethylene. The processes may include introducing a propylene feed stream to a metathesis reactor, and contacting the propylene with a metathesis catalyst in the metathesis reactor to convert the propylene to ethylene and 2-butene. An effluent from the metathesis reactor may be recovered, the effluent including ethylene, 2-butene, and unconverted propylene. The effluent may then be separated in a fractionation system to recover an ethylene fraction, a propylene fraction, a c4 fraction, and a C5+ fraction. The propylene fraction and the C4 fraction may then be fed to the metathesis reactor to produce additional ethylene.

In another aspect, embodiments herein relate to processes for the production of ethylene. The processes may include mixing a propylene feed stream and one or more C3-C5 hydrocarbon containing fractions to form a mixed feed stream. The mixed feed stream may be fed to a metathesis reactor containing a metathesis catalyst for contacting the mixed feed stream with the metathesis catalyst to produce a reaction effluent comprising ethylene, unconverted propylene, 2-butene, 2-pentene, and 2-hexene. The reaction effluent may then be fractionated to recover an ethylene product stream, the one or more C3-C5 hydrocarbon containing fractions, and one or more C6+ fractions.

In yet another aspect, embodiments herein relate to systems for the production of ethylene. The systems may include: a feed stream for providing a propylene feed; a metathesis reactor containing a metathesis catalyst to convert the propylene to ethylene and 2-butene; a fractionation system for separating the ethylene, 2-butene, and unconverted propylene in the metathesis reactor effluent to recover an ethylene fraction, a propylene fraction, a C4 fraction, and a C5+ fraction; one or more flow lines for feeding the propylene fraction and the C4 fraction to the metathesis reactor to produce additional ethylene.

Other aspects and advantages will be apparent from the following description and the appended claims.

DETAILED DESCRIPTION

As noted above, in propylene metathesis, two moles of propylene produce one mole of ethylene and one mole of 2-butene. Ethylene is a more valuable product than butenes, and thus it is desirable to increase the conversion of propylene to ethylene. Embodiments herein may be used to maximize the production of ethylene from propylene.

Propylene metathesis according to embodiments herein may be conducted in a metathesis reaction zone, which may include one or more reactors containing a metathesis catalyst. Where two or more reactors are used, these may be placed in series or in parallel.

A propylene feed stream may be introduced to the metathesis reactor and contacted with the metathesis catalyst to convert propylene to ethylene and 2-butene. An effluent from the metathesis reactor may then be recovered, and may include the aforementioned ethylene and 2-butene, as well as other byproducts and unreacted (unconverted) propylene.

The effluent may then be fed to a fractionation system, including one or more distillation columns and/or extractive distillation columns, for example, and separated into two or more fractions. The two or more fractions may include an ethylene product fraction and one or more fractions selected from a C3 fraction, a C4 fraction, a C5+ fraction, or various fractions including two or more carbon numbers, such as a C3-C4 fraction, a C4-C5 fraction, or a C3-C5 fraction, for example.

The C3, C4, and/or C5 fractions may then be fed to the metathesis reactor, for reaction along with the propylene feed stream, to produce additional ethylene. Propylene returned from the fractionation section to the reactor may react via autometathesis to produce additional ethylene and 2-butene. The propylene may additionally react with any 1-butenes or 1-pentenes, for example, to produce ethylene and 2-pentenes or 2-hexenes, respectively.

Propylene feed streams useful in embodiments herein may include dilute propylene streams, containing up to 50% propane, for example. In some embodiments, the propylene feed stream may include a low purity propylene feed, including 60-95 wt % propylene. In other embodiments, the propylene feed stream may include high purity propylene (95-99+ wt % propylene). A propane/propylene feed stream, in various embodiments, may contain at least 65 wt % propylene, at least 70 wt %, at least 75 wt %, at least 80 wt %, at least 85 wt %, at least 90 wt %, such as between 80 wt % and 95 wt %, or such as between 85 wt % and 90 wt % propylene, and may be fed to a metathesis reactor or reaction zone. In other embodiments, the propylene feed stream may be a polymer-grade propylene stream, which may have at least 98 wt %, at least 99 wt %, at least 99.5 wt %, or at least 99.8 wt % propylene.

The production of ethylene from such propylene feeds may be performed by metathesis of the propylene. In some embodiments, the production of ethylene may be conducted by a combination of metathesis and isomerization. In such embodiments, the isomerization and metathesis may be conducted in segregated reaction zones, in the same or different reactors, or may be conducted in the same reaction zone using a mixed catalyst system or a bifunctional catalyst.

Conditions in the metathesis reactor or the combined metathesis/isomerization reactor for the conversion of propylene to ethylene for metathesis may include temperatures in the range from 500° C. to 6500° C., and pressures in the range from 0 barg to 40 barg. The reactors may be operated such that the reaction temperature is within the range from about 500° C. to about 6000° C.; within the range from about 2000° C. to about 4500° C. in other embodiments; and from about 2500° C. to about 4000° C. in yet other embodiments. Pressures in the reactor may be, in some embodiments, between 5 and 15 bar, for example. The isomerization and metathesis reactions may be performed at a weight hourly space velocity (WHSV) in the range from about 2 to about 200 in some embodiments, and from about 6 to about 40 in other embodiments.

The reactions may be carried out by contacting the olefin(s) with the isomerization and/or metathesis catalysts in the liquid phase or the gas phase, depending on structure and molecular weight of the olefin(s). If the reaction is carried out in the liquid phase, solvents or diluents for the reaction can be used. Aliphatic saturated hydrocarbons, e.g., pentanes, hexanes, cyclohexanes, dodecanes and aromatic hydrocarbons such as benzene and toluene are suitable. If the reaction is carried out in the gaseous phase, diluents such as saturated aliphatic hydrocarbons, for example, methane, ethane, propane, normal and branched C4, C5, alkanes and/or substantially inert gases, such as nitrogen and argon, may be present. For high product yield, the reactions may be conducted in the absence of significant amounts of deactivating materials such as water and oxygen.

The contact time needed to obtain a desirable yield of reaction products depends upon several factors such as the activity of the catalyst, temperature, pressure, and the structure of the olefin(s) to be isomerized and/or metathesized. Length of time during which the olefin(s) are contacted with catalyst can vary between 0.1 seconds and 4 hours, preferably from about 0.5 sec to about 0.5 hrs. The isomerization and metathesis reactions may be conducted batch-wise or continuously with fixed catalyst beds, slurried catalyst, fluidized beds, or by using any other conventional contacting techniques.

The catalyst contained within the metathesis reactors may be any known metathesis catalyst, including oxides of Group VIA, Group VIIA, and Group VIIIA metals on supports. Catalyst supports can be of any type and could include alumina, silica, mixtures thereof, zirconia, magnesia, titania, MOF (metal organic framework) compounds, and zeolites. In some embodiments, the metathesis catalyst is tungsten oxide on silica.

The double bond isomerization catalyst may be any known double bond isomerization catalyst. In some embodiments, the double bond isomerization catalyst may be one of magnesium oxide, calcium oxide, aluminum oxide, or mixed Mg-Al oxides (e.g, hydrotalcite-derived mixed oxides), among other possible catalysts.

In some embodiments, the double bond isomerization catalyst may be an alumina-titania catalyst. The catalyst may be a y-alumina-titania crystalline mixture including active sites that catalyze the positional isomerization of olefins, and may be in the form of pellets, spheres, extrudates, and the like, and will typically have an effective diameter of 0.5 mm to 5 mm, such as in the range from 1 mm to 4 mm, or in the range from 2 mm to 3 mm. In some embodiments, the alumina-titania catalyst may have a composition of titanium with a lower limit of 0.01, 1, 2, 3, 4, 5, 10, 15, 20, or 25 to an upper limit of 15, 20, 25, 30, 35, 40, 45, or 50 wt %, where any lower limit may be combined with any upper limit. y-Alumina-titania catalyst herein may have a surface area in some embodiments greater than 200 m$^2$/g, in other embodiments greater than 250 m$^2$/g, in other embodiments greater than 300 m$^2$/g, in other embodiments greater than 350 m$^2$/g, and in other embodiments greater than 400 m$^2$/g. The y-alumina-titania catalysts may be tolerant of oxygenated species that are typically considered a poison, such as to MgO type catalysts, may act as an oxygenate scavenger protecting downstream catalyst beds, and in some embodiments may have activity for dehydration of alcohols in addition to isomerization activity. The y-alumina-titania catalysts may also be more forgiving with respect to cyclopentene purity of the feed, and may allow greater than 5 wt %, greater than 7.5 wt %, or even greater than 10 wt % cyclopentene to be present in the feed, potentially negating typical upstream processes required to remove cyclopentene from the feed. These y-alumina-titania catalysts may be used alone, such as in an isomerization only reactor or in an isomerization catalyst bed in a segregated OCU, or may be used in admixture with other isomerization catalysts or metathesis catalysts.

Figure 1:
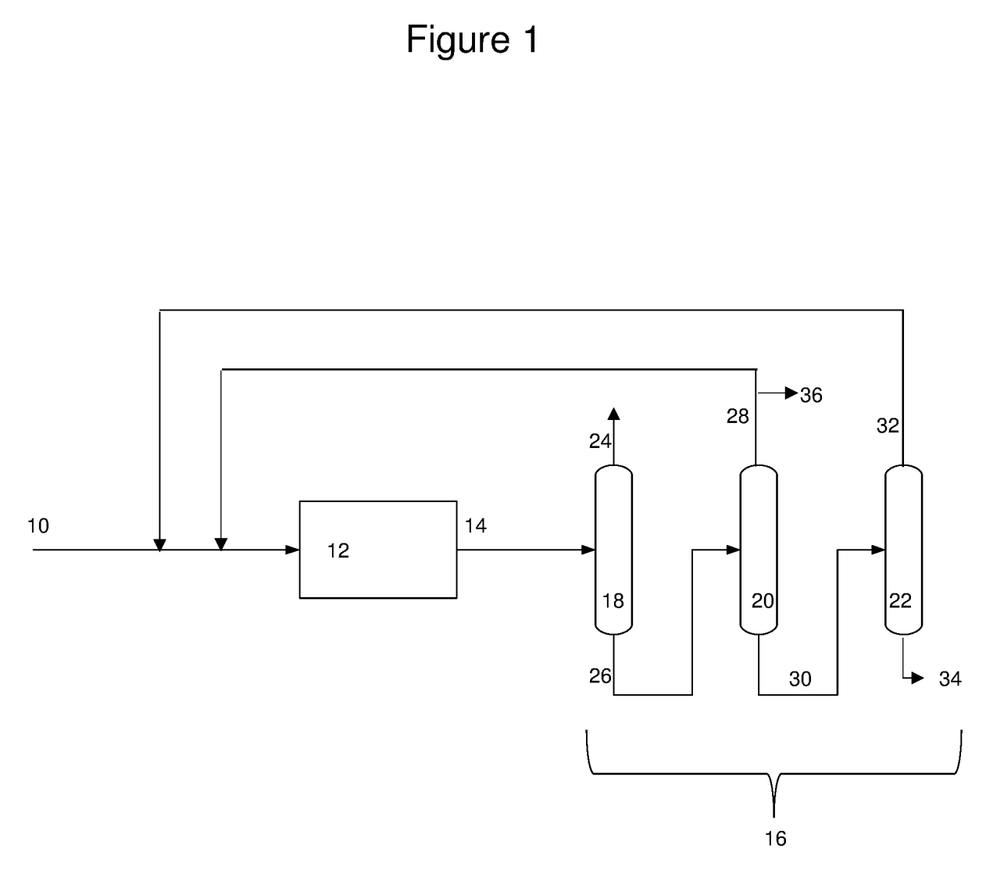
FIGS. 1-6 are simplified flow diagrams of processes according to embodiments herein.

Referring now to FIG. 1, a simplified process flow diagram of systems for producing ethylene according to embodiments herein is illustrated. A propylene feed stream 10 is fed into an olefin conversion unit (OCU) 12, which may include a reaction zone containing a metathesis catalyst or a mixed metathesis/isomerization catalyst. The OCU may also include an isomerization reaction zone, where the isomerization and metathesis reactions are performed in segregated reaction zones, in the same or different reactors.

The propylene in the feed may react to form ethylene and 2-butene, among other reaction products and byproducts which may be recovered in OCU effluent 14. The effluent 14 may then be fed to a fractionation zone 16 to recover the desired ethylene product.

Fractionation zone 16 may include two or more distillation columns to recover desired hydrocarbon fractions. For example, fractionation zone 16 may include a deethylenizer to recover the ethylene product, as well as one or more of: (i) a depropanizer for recovering and returning unreacted propylene to the olefin conversion unit for production of additional ethylene, (ii) a debutanizer for recovering a C4 fraction, (ii) a depentanizer for recovering a C5 fraction or a mixed C4/C5 fraction, and (iii) a dehexanizer for recovering a heavies fraction (bottoms) and one or more of a C6 fraction, a C5/C6 fraction, or a C4/C5/C6 fraction.

As illustrated in FIG. 1, fractionation zone 16 includes a deethylenizer 18, a depropanizer 20, and a debutanizer 22. The deethylenizer 18 may be used to recover an overhead fraction 24 comprising the product ethylene and a bottoms fraction 26 comprising C3+ hydrocarbons. The C3+ hydrocarbons in bottoms fraction 26 may then be separated in the depropanizer 20 to recover a C3 overheads fraction 28 and a C4+ bottoms fraction 30. Subsequently, the C4+ bottoms fraction may be separated in debutanizer 22 to recover an overheads fraction 32 including C4 hydrocarbons and a bottoms fraction 34 including C5+ hydrocarbons. Each of propylene fraction 28 and butenes fraction 32 may be returned to the olefin conversion unit for metathesis of the propylene to produce ethylene and butenes and metathesis of the butenes to produce additional ethylene and pentenes. As the propylene feed results in a relatively high concentration of propylene, the reaction equilibrium favors the reactions of the propylene with the butenes. Pentenes produced in the metathesis reactor may also react with propylene to form ethylene and hexenes. Other heavier olefins may also be formed, recovered with heavies fraction 34. To avoid buildup of propane within the system, a C3 purge stream 36 may be withdrawn. The butenes, however, may be reacted to extinction in some embodiments, and thus a C4 purge stream may not be required (optional).

Figure 2:
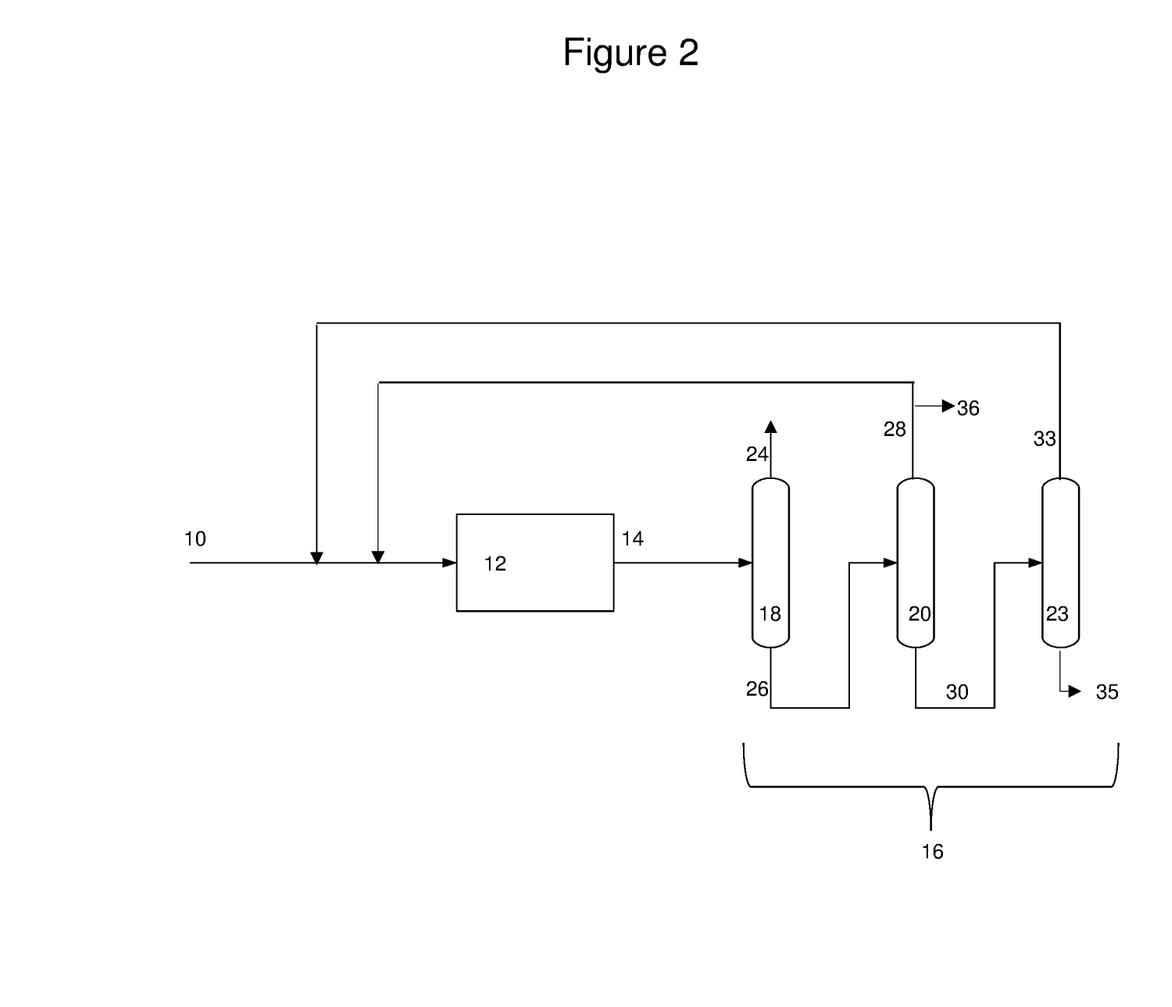

As illustrated in FIG. 2, where like numerals represent like parts, fractionation system 16 may include a deethylenizer 18, a depropanizer 20, and a depentanizer 23. The deethylenizer 18 may be used to recover an overhead fraction 24 comprising the product ethylene and a bottoms fraction 26 comprising C3+ hydrocarbons. The C3+ hydrocarbons in bottoms fraction 26 may then be separated in the depropanizer 20 to recover a C3 overheads fraction 28 and a C4+ bottoms fraction 30. Subsequently, the C4+ bottoms fraction may be separated in depentanizer 23 to recover an overheads fraction 33 including C4-C5 hydrocarbons and a bottoms fraction 35 including C6+ hydrocarbons. Each of propylene fraction 28 and C4/C5 fraction 33 may be returned to the olefin conversion unit for metathesis of the propylene to produce ethylene, metathesis of the butenes and metathesis of the pentenes to produce additional ethylene and hexenes. As the propylene feed results in a relatively high concentration of propylene, the reaction equilibrium favors the reactions of the propylene with the butenes and pentenes. Other heavier olefins may also be formed, recovered with heavies fraction 34. To avoid buildup of propane within the system, a C3 purge stream 34 may be withdrawn. Thep butenes and pentenes, however, may be reacted to extinction in some embodiments, and thus a C4 purge stream may not be required (optional).

When the 2-butenes formed (or n-butenes formed, in the presence of a double-bond isomerization catalyst, along with the metathesis catalyst), are returned back to the propylene metathesis reactor, additional moles of ethylene are generated by the reaction of propylene and n-butenes to form ethylene and n-pentenes. In this process, n-pentenes are created as a by-product along with the ethylene. The n-pentenes that are formed can also be returned back to the same propylene metathesis reactor, to create additional ethylene and form n-hexenes, by the reaction of propylene and n-pentenes to form ethylene and n-hexenes. As illustrated in the embodiments of FIGS. 1 and 2, by returning the n-butenes and n-pentenes back to the propylene metathesis reactor, additional ethylene product is generated along with the formation of n-hexenes as a by-product.

Figure 3:
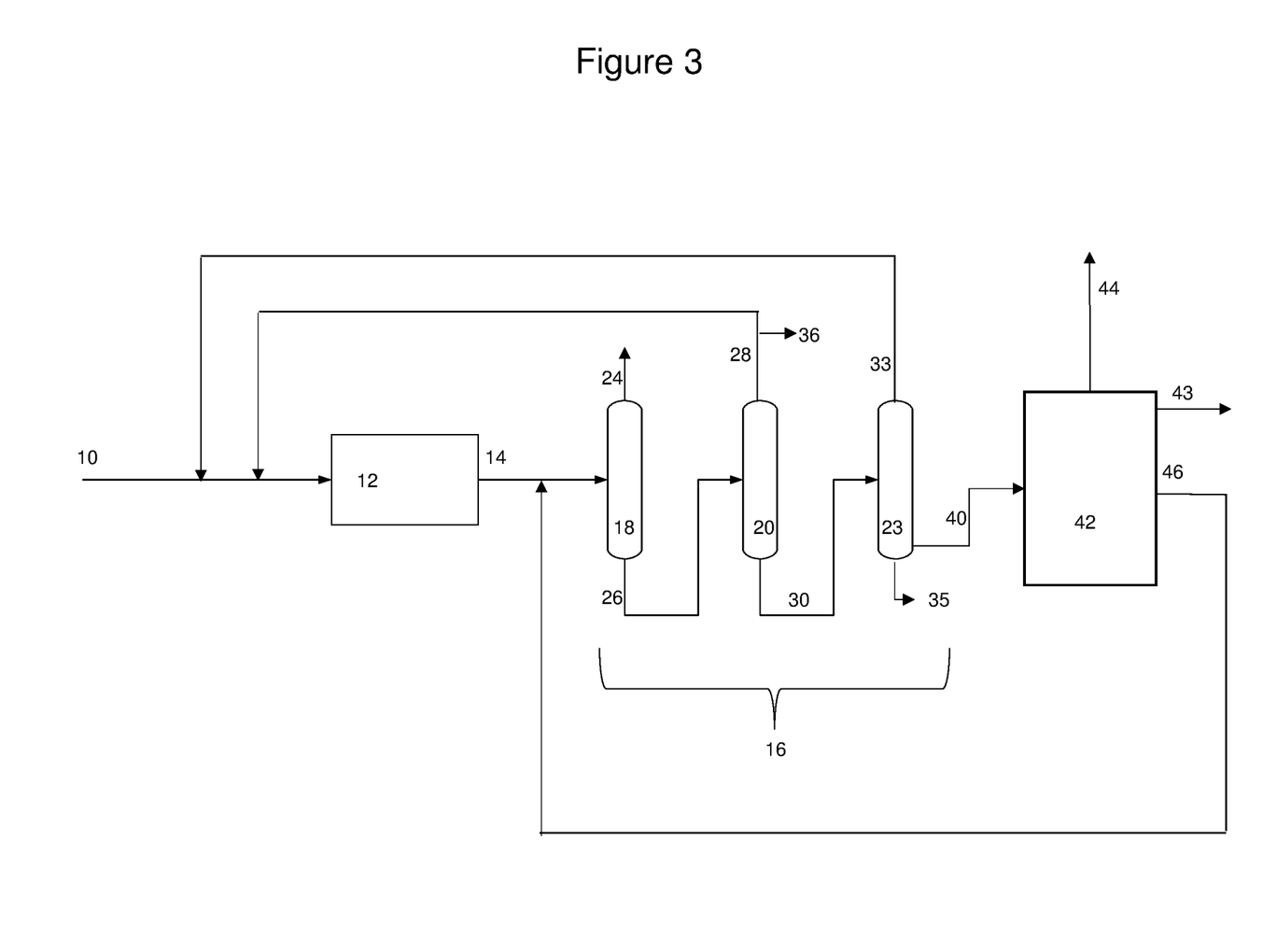

To further maximize the ethylene production, the n-hexenes can be sent to a steam cracker. This embodiment is illustrated in FIG. 3, where like numerals represent like parts. The depentanizer 23 may include a C6-rich side draw 40, which may be fed to a steam cracker 42. Alternatively, or additionally, the C6+ bottoms fraction 35 may be fed to the steam cracker 42. In the steam cracker, thermal cracking produces a product stream containing predominantly ethylene and propylene, and other heavier cracked products. Further, a small C4/C5 purge 47 may be withdrawn from stream 33. While not illustrated, in some embodiments, the C6 olefins may be hydrogenated and fed to the cracker as an alkane.

Figure 6:
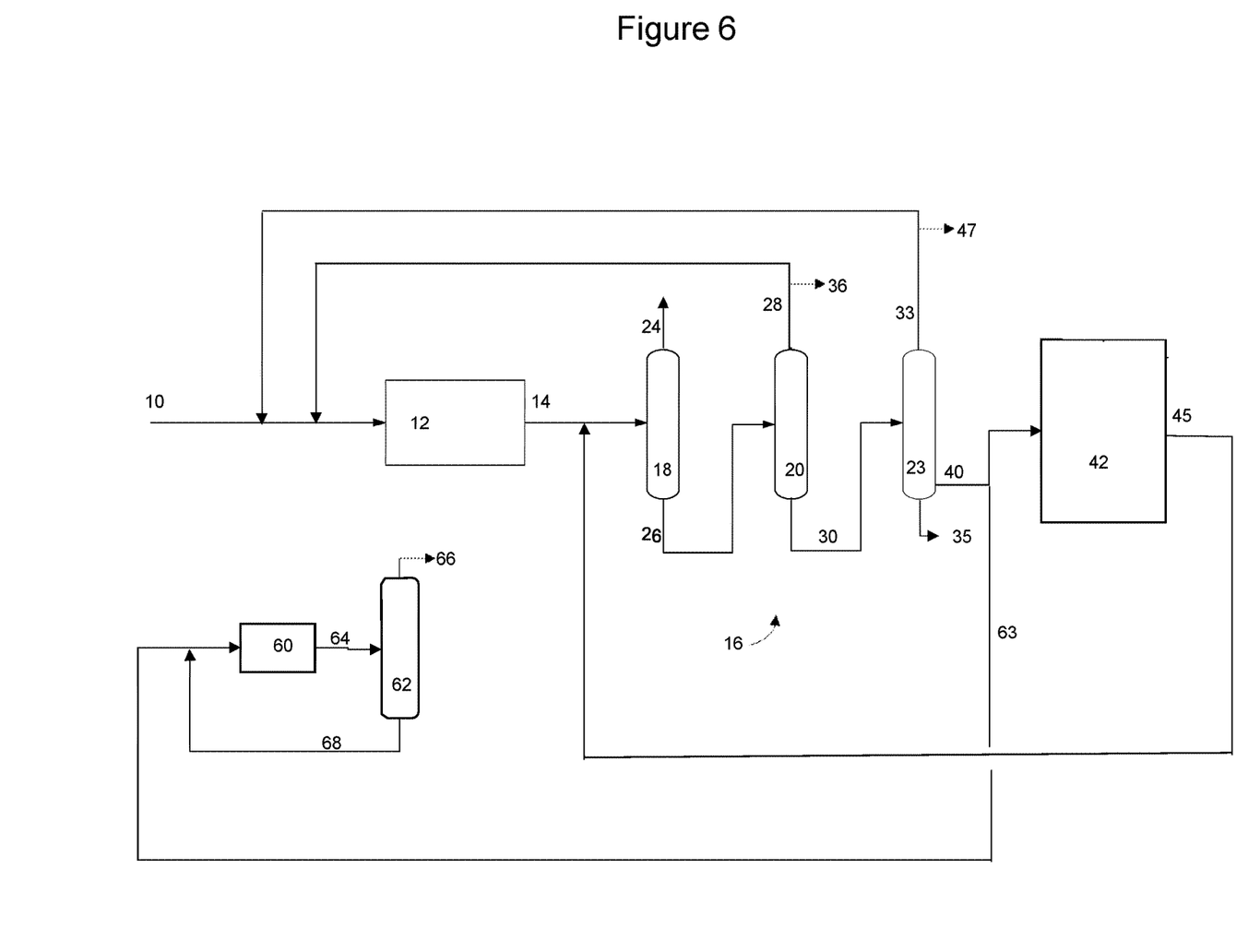

The steam cracker effluent may be fractionated in a separate fractionation system (not illustrated), or returned to fractionation system 16 for common separation with the metathesis effluent via line 45 (FIG. 6). As illustrated in FIG. 3, the steam cracker system 42 may include a lights column (not illustrated) to recover a lights (methane) stream 43, a deethylenizer (not illustrated) to recover an ethylene stream 44 (ethylene produced in the steam cracker), and a depentanizer (not illustrated), to recover C3-C5 hydrocarbon stream 46. The C6+ hydrocarbons recovered in the steam cracker effluent may be recycled to the steam cracker for further conversion and/or may be purged from the system. Ethylene product produced in the steam cracked adds to the overall ethylene product yield. Propylene, n-butenes and n-pentenes formed in the steam cracker can be recycled back to the propylene metathesis reactor, for additional ethylene production. Other than the light hydrocarbon loss (methane) and the heavier (C6+ hydrocarbon) loss, a significant portion of the propylene can be converted to ethylene in this process flow scheme.

Figure 4:
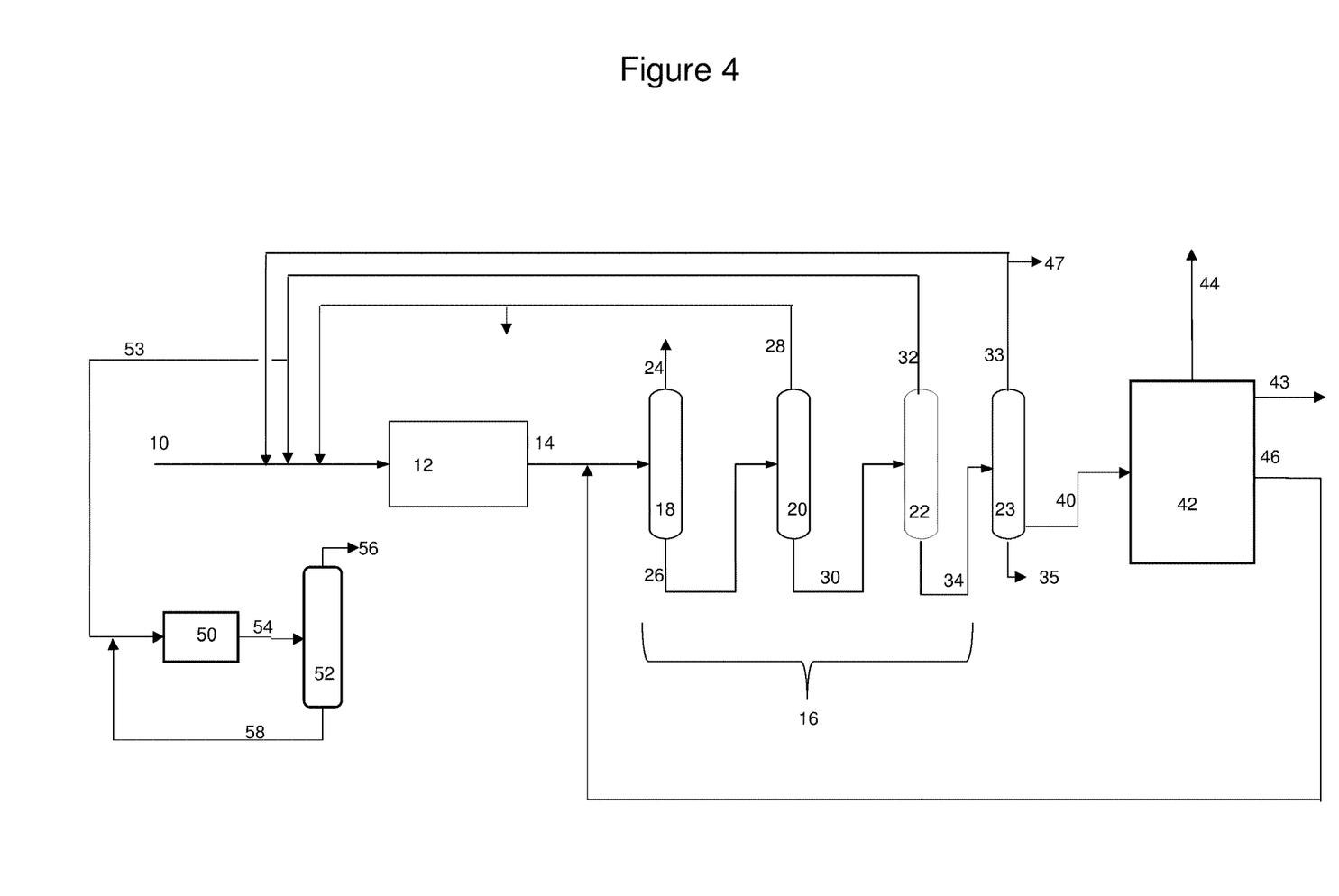

FIG. 4 illustrates another process configuration for producing ethylene according to embodiments herein, where like numerals represent like parts. In this embodiment, fractionation system 16 includes a dethylenizer 18, a depropanizer 20, a debutanizer 22, and a depentanizer 23. Similar to FIG. 3, the system further includes a steam cracker 42 for converting C6 or C6+ hydrocarbons to additional ethylene. Additionally, the system may include a C4 isomerization reaction system for converting 2-butene to 1-butene. The C4 isomerization reaction system may include a fixed bed reactor 50 and a distillation column 52. A portion 53 of the C4 overheads 32, containing 2-butene, may be withdrawn and fed to the C4 isomerization reactor to convert the 2-butene to 1-butene. The effluent 54 from the isomerization reactor may then be separated to recover a 1-butenes overhead fraction 56 and a 2-butene bottoms fraction 58, which may be recycled to the isomerization reactor for additional conversion. Alternatively, the fixed bed reactor may be substituted with or supplemented with a catalytic distillation reactor for conversion of 2-butene to produce a 1-butene while concurrently separating the reactant and product.

Figure 5:
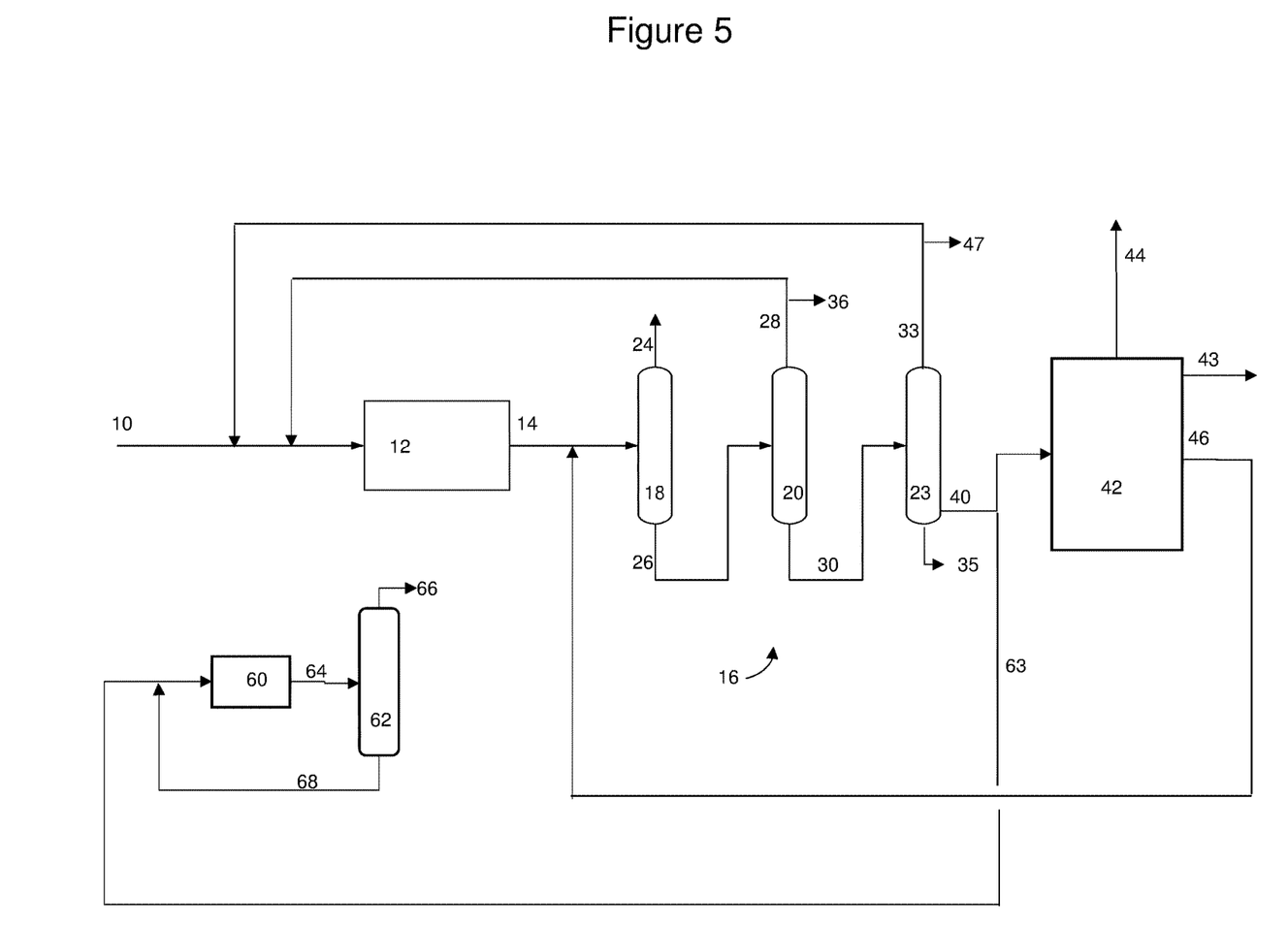

FIG. 5 illustrates another process configuration for producing ethylene according to embodiments herein, where like numerals represent like parts. In this embodiment, fractionation system 16 includes a dethylenizer 18, a depropanizer 20, and a depentanizer 23. In the depentanizer 23, a C4/C5 overheads fraction 33, a C6 side draw fraction 40, and a C6+ bottoms fraction 35 are recovered. Similar to FIG. 3, the system further includes a steam cracker 42 for converting C6 or C6+ hydrocarbons to additional ethylene. Additionally, the system may include a C6 isomerization reaction system for converting 2-hexenes and 3-hexenes to 1-hexene. The C6 isomerization reaction system may include a fixed bed reactor 60 and a superfractionation column 62. A portion 63 of the C6 side draw fraction 40, containing 2-hexene and 3-hexene, may be withdrawn and fed to the C6 isomerization reactor to convert the 2- and 3-hexenes to 1-hexene. The effluent 64 from the isomerization reactor may then be separated to recover a 1-hexenes overhead fraction 66 and a 2- and 3-hexenes bottoms fraction 68, which may be recycled to the isomerization reactor for additional conversion.

In yet other embodiments, both a C4 isomerization system and a C6 isomerization system may be provided to produce both 1-butene and 1-hexene products.

Embodiments herein, as described above, may utilize a single propylene metathesis reactor in conjunction with a steam cracker to achieve the maximization of ethylene yield from all of the propylene produced in the overall process scheme. In a process scheme where maximization of ethylene yield is needed, this process scheme can be utilized to achieve this.

Embodiments herein also enable the steam cracker to be operated at a low severity to produce lesser ethylene and higher propylene and in the process enhance steam cracker run length, as the propylene produced in the cracker can be converted back to ethylene utilizing the propylene metathesis reactor.

Propylene metathesis is known to produce ethylene and n-butenes. However, as described for embodiments herein, the additional conversion of n-butenes and n-pentenes in the propylene metathesis reactor may be utilized as additional feed to further enhance the yield of ethylene. Even further enhancements to the maximization of the ethylene yield may be brought about in embodiments by the conversion of n-hexenes in a steam cracker. The overall process scheme converts most of the propylene to ethylene, and utilizes a single metathesis reactor in conjunction with the steam cracker to achieve this ethylene maximization.

Embodiments herein provide a means of maximizing ethylene yield from propylene metathesis. The propylene metathesis reaction is described by the following metathesis reaction:

Two moles of propylene react in the presence of a metathesis catalyst to form a mole of ethylene and a mole of 2-butene. In various embodiments, the reaction occurs in the temperature range of 2000° C.-5000° C. and pressure range of 0-500 psig. $WO_3/SiO_2$ metathesis catalyst and a double-bond isomerization catalyst may be employed for this reactor. The presence of the double-bond isomerization catalyst converts the 2-butene formed from propylene metathesis into 1-butene. Similarly, the conversion of 2-pentene to 1-pentene is effected by the double-bond isomerization reaction.

When the 2-butenes formed are converted to n-butenes in the presence of the double-bond isomerization catalyst, and contacted with the metathesis catalyst in the the propylene metathesis reactor, additional moles of ethylene are generated, by the reaction of propylene and 1-butene to form ethylene and 2-pentene.

In this process, n-pentenes are created as a by-product along with the ethylene. The n-pentenes that are formed can be further converted in the same propylene metathesis reactor, to create additional ethylene and to form n-hexenes, by the reaction of propylene and 1-pentene to form ethylene and 2-hexene.

So, in the processes according to embodiments herein, reaction of the n-butenes and n-pentenes in the propylene metathesis reactor results in additional ethylene product generated, along with the formation of n-hexenes as a by-product.

To further maximize the ethylene production, the n-hexenes may be sent to a steam cracker. Alternatively, in some embodiments, the C6 olefins may be hydrogenated and fed to the cracker as an alkane. In the steam cracker, thermal cracking produces a product stream containing predominantly ethylene and propylene, and other heavier cracked products and some light hydrocarbons. Ethylene product produced in the steam cracker adds to the increase in the ethylene product yield. Propylene, n-butenes and n-pentenes formed in the steam cracker can be converted in the propylene metathesis reactor, for additional ethylene production. Other than the light hydrocarbon loss (methane) and the heavier (C6+ hydrocarbon) loss, a significant portion of the propylene can be converted to ethylene in the process flow schemes according to embodiments herein.

Embodiments herein thus may utilize a single propylene metathesis reactor in conjunction with a steam cracker to achieve the maximization of ethylene yield from all of the propylene produced in the overall process scheme.

Other embodiments herein include the variation of the process flow scheme to produce 1-hexene comonomer as a second product along with ethylene product. In this configuration, the n-hexenes produced from the metathesis or metathesis/steam cracker process to produce 1-hexene comonomer product. The process includes an n-hexenes isomerization reactor and a 1-hexene superfractionator, with the bottoms of the superfractionator (mostly 2-hexenes, 3-hexenes) recycled back to the n-hexenes isomerization reactor.

Another variant of the process flow scheme according to embodiments herein will produce 1-butene comonomer product. In such embodiments, the n-butenes product from the propylene metathesis reactor may be integrated to produce 1-butene comonomer product along with ethylene. The n-butenes may be sent to a n-butenes isomerization reactor and subsequently a 1-butene superfractionator, with the bottoms of the superfractionator (2-butenes) recycled back to the n-butenes isomerization reactor.

Embodiments herein convert propylene to ethylene via metathesis. Further conversion of n-butenes and/or n-pentenes in the same reactor along with the unconverted propylene is novel and results in the additional ethylene production. By converting the n-butenes and n-pentenes in the propylene metathesis reactor (and converting the n-butenes and n-pentenes to extinction), the two products formed from the reactor in some embodiments are ethylene and n-hexenes. Further, embodiments herein may crack the n-hexenes to from ethylene, propylene, butenes, pentenes and some heavier components. The C3, C4, and C5 olefins formed in the cracker can be sent to the propylene metathesis unit. So, essentially, other than some heavies loss and CH4 loss in the steam cracker, most of the original propylene may be converted to ethylene according to embodiments herein. This may result in essentially the maximization of the ethylene production from the propylene stream. On a mass basis, embodiments herein may be used to convert greater than 40% propylene, on a mass basis, to ethylene. For example, embodiments according to the process of FIG. 1 may be used to result in 42%-48% conversion of propylene to ethylene, according to simulation results. Embodiments according to the process of FIG. 2 may be used to result in 45%-55% conversion of propylene to ethylene, according to simulation results. Embodiments according to FIGS. 3-5 may be used to result in 65%-75% conversion, on a mass basis, to ethylene, based on simulation results.

The addition of 1-hexene as a product and/or 1-butene as a product adds to the flexibility of the process scheme. A stream of n-hexenes generated in the process may be utilized to make the 1-hexene product. Similarly, a stream of n-butenes may be utilized to make the 1-butene product. 1-Butene and 1-hexene are co-monomers in polyethylene production, and may be of value.

Embodiments herein provide a unique way to increase the ethylene yield from a propylene stream, which was not possible with the current commercial reactor or knowledge base. As noted above, propylene metathesis creates one mole of ethylene (28 g/mol) from two moles of propylene (42+42). N-butenes (56 g/mol) as the second product is less valuable, and on a mass basis only 33.3% of the propylene ends up as ethylene, and the rest is n-butenes. Embodiments herein completely turn this around to create a high percentage ethylene stream with minimal side products, such as heavies and methane, where propylene utilization may be as high as 90%, on a mass basis.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed:

1. A system for the conversion of propylene to ethylene, the system comprising:
    a feed stream for providing a propylene feed;
    a metathesis reactor containing a metathesis catalyst to convert the propylene to ethylene and 2-butene, and produce a metathesis reactor effluent comprising ethylene, 2-butene, and unconverted propylene, 2-pentene, and 2-hexene;
    a first fractionation system for separating the ethylene, 2-butene, and unconverted propylene in the metathesis reactor effluent to recover an ethylene fraction, a propylene fraction, a C4 fraction, and a C5+ fraction;
    one or more flow lines for feeding the propylene fraction and the C4 fraction to the metathesis reactor to produce additional ethylene;
    a second fractionation system for separating the C5+ fraction into a C5 fraction, a C6 fraction, and a C6+ fraction; and
    a steam cracker for cracking at least a portion of one or more of the C6+ fraction, C6 fraction, or a hydrogenated product thereof to produce a cracker effluent comprising ethylene, propylene, butenes, and/or pentenes.

2. The system of claim 1, further comprising:
    a flow line for feeding the C5 fraction to the metathesis reactor to produce additional ethylene.

3. The system of claim 1, further comprising:
    a third fractionation system for separating the cracker effluent to recover an ethylene fraction and one or more C3-C5 fractions.

4. The system of claim 3, further comprising a flow line for feeding the one or more C3-C5 fractions to the metathesis reactor to produce additional ethylene.

5. The system of claim 1, further comprising a flow line for feeding at least a portion of the cracker effluent to the first fractionation system.

6. The system of claim 1, further comprising:
    an isomerization reactor containing an isomerization catalyst for converting at least a portion of the 2-butene contained in the C4 fraction to 1-butene.

7. The system of claim 6, further comprising a flow line for feeding the 1-butene to the metathesis reactor.

8. The system of claim 1, further comprising:
    an isomerization reactor containing an isomerization catalyst for converting at least a portion of the 2-hexene and 3-hexene contained in the C6 fraction, C6+ fraction, or both, to 1-hexene.

9. A system for the production of ethylene, comprising:
    a metathesis reactor containing a metathesis catalyst, the metathesis reactor configured for receiving a mixed feed stream comprising a propylene feed stream and one or more C3-C5 hydrocarbon containing fractions, and contacting the mixed feed stream with the metathesis catalyst to produce a reaction effluent comprising ethylene, unconverted propylene, 2-butene, 2-pentene, and 2-hexene;
    a first flow line for feeding the reaction effluent to a deethylenizer to separate the reaction effluent into an ethylene product stream and a C3+ fraction;
    a second flow line for feeding the C3+ fraction to a depropanizer to separate the C3+ fraction into a C3 fraction and a C4+ fraction;
    a third flow line for feeding the C4+ fraction to a debutanizer to separate the C4+ fraction into a C4 fraction and a C5+ fraction;
    a fourth flow line for feeding the C5+ fraction to a depentanizer to separate the C5+ fraction into a C5 fraction and a C6+ fraction; and
    a steam cracker for cracking the C6+ fraction to produce a cracker effluent comprising one or more of ethylene, propylene, butenes, and pentenes; and
    a fifth flow line for feeding the steam cracker effluent to the first flow line with the reaction effluent;
    wherein an overall system is configured for converting propylene to ethylene at greater than 40% on a mass basis.

10. The system of claim 9, wherein the metathesis reactor is configured for receiving a feed stream mixture comprising of one or more C3-C5 hydrocarbon containing fractions including one or more of the following fractions: a C3 fraction, a C4 fraction, a C5 fraction, a C3-C4 fraction, a C4-C5 fraction, and/or a C3-C5 fraction.

11. The system of claim 9, further comprising:
    one or more flow lines for recycling at least a portion of one or more of the C3 fraction, the C4 fraction, and the C5 fraction as one or more of the C3-C5 hydrocarbon containing fractions to produce additional ethylene.

12. The system of claim 10, further comprising:
    an isomerization reactor containing a C4 isomerization catalyst configured for converting a portion of the 2-butene in the C4 fraction to 1-butene.

13. The system of claim 12, further comprising a recycle line feeding the 1-butene to the metathesis reactor.

14. A system for the production of ethylene, comprising:
    a metathesis reactor containing a metathesis catalyst, the metathesis reactor configured for receiving a mixed feed stream comprising a propylene feed stream and one or more C3-C5 hydrocarbon containing fractions, and contacting the mixed feed stream with the metathesis catalyst to produce a reaction effluent comprising one or more of ethylene, unconverted propylene, 2-butene, 2-pentene, and 2-hexene;
    a fractionation system comprising a deethylenizer, a depropanizer, a debutanizer, and depentanizer configured for receiving the reaction effluent and producing an ethylene product fraction, a C3 fraction, a C4 fraction, a C5 fraction, a C6 fraction, and a C6+ fraction;
    a steam cracker configured for cracking at least a portion of the C6 fraction, C6+ fraction, or both, to produce a cracker effluent comprising ethylene, propylene, butenes, pentenes, or a combination thereof; and
    a flow line for feeding the steam cracker effluent to the fractionation system for fractionation with the reaction effluent;
    wherein the overall system is configured for converting greater than 40% of propylene to ethylene on a mass basis.

15. The system of claim 14, wherein the metathesis reactor is configured for receiving a feed comprising of one or more C3-C5 hydrocarbon containing fractions including one or more of a C3 fraction, a C4 fraction, a C5 fraction, a C3-C4 fraction, a C4-C5 fraction, and a C3-C5 fraction.

16. The system of claim 14, further comprising:
a flow line for recycling at least a portion of one or more of the C3 fraction, C4 fraction, and C5 fraction as the one or more C3-C5 hydrocarbon containing fractions to produce additional ethylene.

17. The system of claim 14, further comprising:
an isomerization reactor containing C6 isomerization catalyst configured to receive at least a portion of the C6 fraction, convert a portion of the 2-hexenes and 3-hexenes to 1-hexene, .and produce an isomerization effluent comprising unreacted 2-hexene, unreacted 3-hexene, and 1-hexene.

18. The system of claim 17, further comprising an isomerization effluent fractionation system for separating the isomerization effluent to produce a 2-hexene and 3-hexene fraction and a 1-hexene fraction.

19. The system of claim 18, further comprising a recycle line for recycling at least a portion of the 2-hexene and 3-hexene fraction to the isomerization reactor.

\* \* \* \* \*